US010293273B2

(12) United States Patent
Chen et al.

(10) Patent No.: US 10,293,273 B2
(45) Date of Patent: May 21, 2019

(54) METHOD FOR CONTINUOUS PREPARATION OF HIGH BULK DENSITY METHIONINE CRYSTAL

(71) Applicants: Shandong Nhu Amino Acid Co., Ltd., Weifang, Shandong (CN); Zhejiang University, Hangzhou, Zhejiang (CN); Zhejiang Nhu Co., Ltd., Shaoxing, Zhejiang (CN)

(72) Inventors: Zhirong Chen, Zhejiang (CN); Zhixuan Wang, Weifang (CN); Cong Chen, Weifang (CN); Zhengjiang Wang, Weifang (CN); Cunchao Wang, Weifang (CN); Yin Li, Weifang (CN); Zhixiang Zhang, Weifang (CN)

(73) Assignees: Shandong Nhu Amino Acid Co. Ltd., Shandong (CN); Zhejiang University, Zhejiang (CN); Zhejiang Nhu Co., Ltd., Zhejiang (CN)

( * ) Notice: Subject to any disclaimer, the term of this patent is extended or adjusted under 35 U.S.C. 154(b) by 0 days.

(21) Appl. No.: 15/549,833

(22) PCT Filed: Dec. 23, 2015

(86) PCT No.: PCT/CN2015/098368
§ 371 (c)(1),
(2) Date: Aug. 9, 2017

(87) PCT Pub. No.: WO2016/127707
PCT Pub. Date: Aug. 18, 2016

(65) Prior Publication Data
US 2018/0043281 A1 Feb. 15, 2018

(30) Foreign Application Priority Data

Feb. 12, 2015 (CN) .......................... 2015 1 0078388

(51) Int. Cl.
*B01D 9/00* (2006.01)
*C07C 319/28* (2006.01)
*C07C 323/58* (2006.01)

(52) U.S. Cl.
CPC ......... *B01D 9/0036* (2013.01); *B01D 9/0013* (2013.01); *B01D 9/0027* (2013.01); *B01D 9/0054* (2013.01); *C07C 319/28* (2013.01); *C07C 323/58* (2013.01); *B01D 2009/0086* (2013.01)

(58) Field of Classification Search
CPC .. B01D 9/0013; B01D 9/0027; B01D 9/0036; B01D 9/0054; B01D 2009/0086; C07C 319/28; C07C 323/58
See application file for complete search history.

(56) References Cited

U.S. PATENT DOCUMENTS

| 5,463,120 A | 10/1995 | Giraud et al. |
| 2005/0131111 A1* | 6/2005 | Weckbecker ......... C07C 319/20 524/35 |
| 2011/0061205 A1 | 3/2011 | Scholz et al. |

FOREIGN PATENT DOCUMENTS

| CA | 866570 | 3/1971 |
| CN | 1274717 A | 11/2000 |
| CN | 1589259 A | 3/2005 |
| CN | 1599712 A | 3/2005 |
| CN | 1636975 A | 7/2005 |
| CN | 101602700 A | 12/2009 |
| CN | 101602701 A | 12/2009 |
| CN | 202983275 | 6/2013 |
| CN | 104174181 | 12/2014 |

(Continued)

OTHER PUBLICATIONS

Extended European Search Report and Search Opinion for EP Application No. 15881855.9 (dated Dec. 7, 2017).

(Continued)

*Primary Examiner* — Pancham Bakshi
*Assistant Examiner* — Mark R Luderer
(74) *Attorney, Agent, or Firm* — Fish & Richardson P.C.

(57) ABSTRACT

The present disclosure relates to a method for continuous preparation of high bulk density methionine crystals. The process of the method is as follows: a hydrolysate solution, which is obtained from a reaction of 5-(β-methylmercaptoethyl) hydantoin and a potassium carbonate solution, is mixed with an external circulation material from a DTB neutralization crystallizer having a gas phase neutralization section; after being cooled, the mixture enters a liquid distributor of a neutralization region in the upper part of the crystallizer and is sprayed in the form of liquid droplet or trickle into carbon dioxide gas for neutralization reaction, and then naturally falls into a crystallization region in the lower part to be mixed with a material in the region; the obtained mixture grows on fine crystals in a system to form crystals having larger particle diameters, and meanwhile new crystal nucleuses are formed; in a deposition area in the middle part of the crystallization region, the crystals having larger particle diameters deposits into an elutriation leg, while the fine crystals circulate with the external circulation material, and a part of the external circulation material is used to elutriate the crystals in the elutriation leg, while another part of the same is used to be mixed with the hydrolysate solution; and the crystals in the elutriation leg are separated, washed and dried to obtain the high bulk density methionine product.

12 Claims, 1 Drawing Sheet

(56) References Cited

FOREIGN PATENT DOCUMENTS

| | | |
|---|---|---|
| CN | 104203912 A | 12/2014 |
| CN | 104744326 A | 7/2015 |
| EP | 0780370 | 6/1997 |
| JP | 04169570 A | 6/1992 |
| JP | 1376671 A | 12/2009 |

OTHER PUBLICATIONS

International Search Report dated Mar. 29, 2016 in corresponding PCT application No. PCT/CN2015/098368.

\* cited by examiner

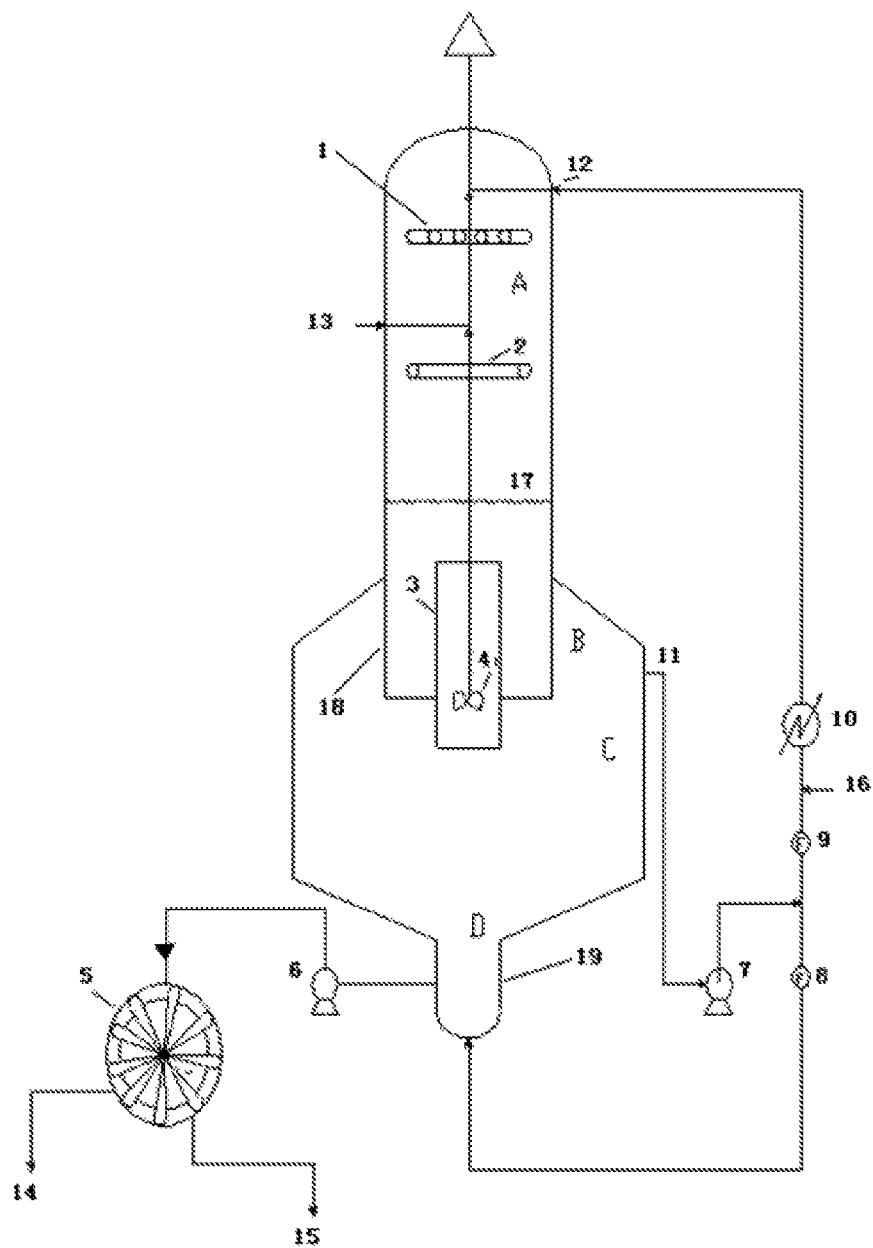

METHOD FOR CONTINUOUS PREPARATION OF HIGH BULK DENSITY METHIONINE CRYSTAL

TECHNICAL FIELD

The present disclosure belongs to the technical field of chemical processing. Specifically, the present disclosure relates to a method for continuous preparation of high bulk density methionine crystals and mainly relates to a new method for methionine crystallization and an improved crystallization device.

RELATED ART

Methionine is one of the essential amino acids for animal growth and is currently the only sulfur-containing amino acid. It is an important feed additive. Methionine products have two forms: solid and liquid. Currently, solid methionine is dominant in the world methionine market.

Currently, methionine is mainly synthesized by chemical methods. Depending on the raw material, the methods mainly include malonate method, acrolein method, and amino lactone method and so on. Major methionine manufacturers such as Adisseo, Soda, Sumimoto and Degussa adopt the acrolein method. The method uses acrolein and methyl mercaptan as raw materials to produce methylthiopropanal and further carry out condensation, hydrolysis and acidifying crystallization to produce methionine. However, different manufacturers have different ways of hydrolysis and acidifying crystallization. Adisseo uses NaOH for hydrolysis to produce methionine sodium and performs crystallization with sulfuric acid to obtain methionine and a by-product of sodium sulfate. Soda uses calcium hydroxide for hydrolysis and performs acidification with hydrochloric acid to obtain methionine and by-products of sodium chloride and calcium carbonate. The crystals produced by the above hydrolysis and acidifying crystallization methods are in the form of powder due to the by-products and impurities. Such crystals cannot be easily separated and will easily generate dust during the drying and packaging process and in use.

On the contrary, the hydrolysis and acidifying crystallization method adopted by Degussa is more advantageous. The process uses hydrocyanic acid and methylthiopropanal for condensation to produce methylthio ethyl hydantoin, and then uses potassium carbonate for hydrolysis and carbon dioxide for acidifying crystallization to obtain methionine, and carbon dioxide and potassium bicarbonate as by-products can be recycled. Thus, the amount of solid waste is significantly reduced, making the method a clean production.

In the process of preparing methionine using the above methods, the acidifying crystallization process has been the focus of study. Due to the use of gaseous carbon dioxide, in the acidification process, methionine suspension has a serious foaming, resulting in excessive crystal nucleus and very fine crystals in the crystallization process. In general, the crystals are scaly crystals that are extremely easily broken. Therefore, the solid-liquid separation is very bad. Serious foaming often interrupts the production process, causing that the production cannot be normally performed.

Currently, there are various studies that use improved equipment, improved processes, or the addition of specific auxiliary substances to avoid foaming.

Patent Document 1, as an early patent, discloses a methionine crystallization process. The process is a hydrolysis process in which 5-(β-methylmercaptoethyl) hydantoin is hydrolyzed with the presence of potassium carbonate, followed by neutralization and crystallization by introducing carbon dioxide into the hydrolyzate solution and separation of the precipitated methionine, and the concentrated filtrate can be applied to the hydrolysis of 5-(β-methylmercaptoethyl) hydantoin. However, the neutralization and crystallization under the condition described by the above patent document has a serious foaming phenomenon. As a result, the methionine crystal finally obtained is scaly and has a low bulk density. If the form of the methionine crystal is to be improved by recrystallization, additional equipment and energy are required, which is not economical.

In order to solve the foaming problem arising from the neutralization with gas carbon dioxide, Patent Document 2 uses the method of adding defoamer in the aqueous solution of methionine alkali metal salts till the concentration of the defoamer is 1000-10000 ppm. Thus, the obtained methionine crystals are porous spherical crystals with the particle diameters within the range of 100-200 μm. There are adhering substances and mother liquor residues in the micropores. In order to obtain a product meeting with the market quality requirements, a large amount of water is needed for washing, which increases the energy consumption and reduces the economy of the process.

Patent Document 3 also uses additives (glutenin, polyvinyl alcohol, methylcellulose and the like) to control the foaming. It points out that a portion of methionine dissolved in the mother liquor during the hydrolysis process forms a methionine polymer that affects the crystalline form of the crystals precipitated during the crystallization and recrystallization. The methionine polymer is decomposed by heating the hydrolysate solution at 160 to 200° C. for 1 to 5 hours, so as to control the amount of the polymer. In the methionine crystal method described above, the resulting crystals are in the form of granules or thick plates having a bulk density of 625 kg/m$^3$. In this document, though the methionine polymer is hydrolyzed by heating the hydrolysate solution, the bulk density of the obtained crystal particles is still not high. Moreover, heating the hydrolyzate solution for a long time increases energy consumption and reduces the production capacity of the production plant.

Patent Document 4 proposes to use a crystallization vessel with a draft tube to obtain methionine crystals by semi-batch crystallization. The process includes neutralizing and crystallizing a 15-40% of the methionine aqueous solution together with a coagulant (sorbitan laurate, polyvinyl alcohol or hydroxypropyl methyl cellulose) in batches for 20-40 min to make the seed crystals grow, then adding the remaining 60-85% of the methionine aqueous solution for continuous neutralization and crystallization for 40-90 min to make the crystals grow. The bulk density of the methionine crystal obtained under the conditions described in this document is 550 kg/m$^3$, which is still not high.

In Patent Document 5, it is proposed that the amount of the by-product methionine polymer in the hydrolyzate solution can be reduced by non-agitation hydrolysis in the first reactor and heating in the second reactor; polyvinyl alcohol is used as the flocculant while the mother liquor for primary crystallization is applied to the hydrolyzate solution to recycle, thereby obtaining a methionine crystal having a high bulk density. The bulk density of methionine crystals obtained is 703 kg/m$^3$ at the crystallization temperature of 10-30° C. and under the carbon dioxide pressure of 0.1-1 MPa. In this process, by heating the hydrolysate solution twice, the bulk density of the crystals merely increases by 5% as compared with the comparative examples, but the equipment needed and the energy consumption increases.

Patent Document 6 uses a vacuum crystallization method to recrystallize a crude methionine to increase the bulk density of the crystal. The process includes dissolving crude methionine with a solvent and an additive at 100° C., feeding the dissolved matters into a vacuum crystallizer, controlling the temperature of the crystallizer via a degree of vacuum, the temperature for first crystallization being controlled at 60-70° C. and the temperature for second crystallization being controlled at 30-50° C. The methionine crystals finally obtained have a bulk density of 640 kg/m$^3$. However, in the step of recrystallization, the crude methionine need to be reheated for dissolving and cooled, followed by a great amount of liquid circulation which increases the energy consumption and reduces the economy of the process.

In addition, many other patents use additives to eliminate the foaming phenomenon during methionine crystallization. Patent JP10306071 provides a method for eliminating foams, in which methionine is crystallized when the potassium salt solution of methionine is neutralized with an acid in the coexistence of glutenin. JPS43-22285 uses a crystallization method in which methionine salt solution is neutralized and crystallized in the coexistence of soluble cellulose derivatives so as to eliminate foams. JPS43-24890 uses a method in which methionine salt solution is neutralized and crystallized in the coexistence of alcohols, phenols and ketones so as to eliminate foams. JPS46-19610 uses a method in which methionine salt solution is neutralized and crystallized in a solution added anionic and nonionic surfactants so as to eliminate foams. JP2921097 discloses a method in which a potassium salt solution of methionine is neutralized and crystallized in the coexistence of polyvinyl alcohol by absorbing carbon dioxide gas so as to eliminate foams.

As shown above, when methionine salt solution is neutralized and crystallized with carbon dioxide, the foaming phenomenon is a significant factor affecting the results of the neutralization and crystallization during the crystallization process. In order to avoid or reduce the foaming phenomenon so as to obtain ideal crystals, most of the prior arts adds defoamers, flocculants and other additives during the crystallization process. A part of these additives will attach to the surface of the crystals and be brought out by the methionine products, while the rest remains in the mother liquor to be recycled together with the mother liquor. The recycling of the later part of the additives will change the proportion of the additives in the mother liquor or will be deteriorated to unknown material due to the heat, thereby affecting the subsequent neutralization and crystallization process and increasing instability in the neutralization and crystallization process. In addition, methionine crystal products of high bulk density cannot be obtained merely by adding additives. Some patent documents describe using recrystallization steps to enhance the bulk density of the methionine crystals. But the recrystallization process requires additional equipment and energy consumption, which reduces the economy of the production process.

DOCUMENTS OF THE PRIOR ART

Patent Document 1: JPS54-9174
Patent Document 2: DE19547236
Patent Document 3: CN1589259
Patent Document 4: CN1274717
Patent Document 5: CN101602701
Patent Document 6: WO2013139562

SUMMARY

Problem to be Solved

The present disclosure intends to solve the following technical problem existing in various production methods of methionine crystal in the prior art: foams are easily generated, the bulk density is not high, and the use of additives affects the crystallization process. By using a DTB neutralization crystallizer having a gas phase neutralization section, the neutralization in the liquid phase that is easy to generate a foaming phenomenon is transferred to be carried out in a gas phase, so as to essentially eliminate the foaming problem in the neutralization process. Meanwhile, by controlling the oversaturation in the crystallization process, formation of crystal nucleus is effectively controlled, thereby obtaining methionine products of high bulk density.

Solution for Solving the Problem

One of the technical solutions of the present disclosure is about a method for continuous preparation of high bulk density methionine crystals, the method comprising the following steps:

(1) mixing a hydrolyzate solution containing potassium methionine obtained from a reaction of 5-(β-methylmercaptoethyl) hydantoin and a potassium carbonate solution with an external circulation material from a DTB neutralization crystallizer having a gas phase neutralization section to form a mixture material; the mixture material entering a liquid distributor of a neutralization region in an upper part of the crystallizer after being cooled and being sprayed in the form of liquid droplet or trickle to gas-liquid contact area to carry out neutralization reaction with carbon dioxide gas so that obtaining a neutralization solution containing methionine;

(2) making the neutralization solution naturally fall into a crystallization region in the lower part of the crystallizer to form crystals in the crystallization region, and then making the crystals having larger particle diameters deposit into a elutriation leg in a deposition area in the middle part of the crystallization region;

(3) feeding the methionine crystals in the elutriation leg through a crystal mush pump into a rotary drum filter to be subjected to separation, washing and drying to obtain methionine products;

wherein the external circulation material is initially a saturated methionine solution.

The bulk density of the high bulk density methionine crystals is at least 800 kg/m$^3$.

Preferably, a hydrolyzate solution containing potassium methionine obtained by a reaction of 5-(β-methylmercaptoethyl) hydantoin with a potassium carbonate solution is pre-cooled, and then mixed with an external circulation material of the same temperature from the neutralization crystallizer to form a mixture material.

Further, preferably, the formation of the crystals includes the following step: the neutralization solution enters the crystallization region and is stirred in the crystallizer to be mixed with the material in the crystallization region, and fine crystals formed in the system grow to form crystals having a larger particle diameter; meanwhile, since the methionine solution is in a state of oversaturation, new crystal nucleus can be formed.

Further, preferably, in the deposition area of the crystallization region, fine crystals and a part of the methionine solution enter the external circulation pipe to be cooled and circulated; a part of the external circulation material is used to wash the crystals in the elutriation leg while another part of the same is used to be mixed with the hydrolyzate solution containing potassium methionine.

Further, preferably, the DTB neutralization crystallizer having a gas phase neutralization section has a gas phase space at an upper part, and a liquid distributor and a gas distributor are provided so that the liquid as a dispersed phase is subjected to a gas-liquid neutralization reaction in a carbon dioxide gas as a continuous phase.

The volume ratio of the reaction solution (hydrolysate solution) containing potassium methionine entering the outer circulation pipe of the DTB neutralization crystallizer having a gas phase neutralization section to the outer circulation solution is 1:5-50, preferably 1:10-30, and the temperature of the mixed material is reduced by a cooler by 0.5-5° C., preferably by 1-3° C. and is stabilized at 20-40° C. after cycle cooling.

The volume ratio of the outer circulation solution entering the elutriation leg of the DTB neutralization crystallizer having a gas phase neutralization section to the output volume of the crystal mush is 1-5:1 and preferably 1.5-4:1.

The agitation rate in the crystallization region of the DTB neutralization crystallizer having a gas phase neutralization section is 50-500 rpm, preferably 100-300 rpm.

The temperature of the crystallization region of the DTB neutralization crystallizer having a gas phase neutralization section is 10-40° C., preferably 20-30° C.

The hydrolyzate solution containing potassium methionine stays in the DTB neutralization crystallizer having a gas phase neutralization section for 0.3-3 hours, preferably 0.5-2 hours. The flow rate of the hydrolyzate solution containing potassium methionine entering the neutralization crystallizer is 0.333-3.33 $m^3/h$ and preferably 0.5-2 $m^3/h$.

The pressure of the gas-phase carbon dioxide in the DTB neutralization crystallizer having a gas phase neutralization section is 0.3-1.2 Mpa and preferably 0.4-1.0 Mpa.

The present disclosure further provides a DTB neutralization crystallizer having a gas phase neutralization section for continuous preparation of high bulk density methionine crystals, comprising:

(1) a liquid distributor for forming the liquid droplets or trickles of mixed liquor containing potassium methionine and a gas distributor for supplying carbon dioxide gas that are provided in a neutralization region at an upper part, (2) a liquid guide shell and a stirrer provided in the middle part, (3) a crystal deposition area provided at a lower part, which includes a elutriation leg for depositing crystal, (4) an external circulation system, partially for being supplied to the elutriation leg, and partially for being mixed with the hydrolyzate solution containing potassium methionine and then circulating supply to the guide shell with the baffle at the material inlet of the neutralization crystallizer.

Further, the DTB neutralization crystallizer having a gas phase neutralization section further comprises a rotary drum filter for separating and washing the crystal mush from the elutriation leg.

The present application is characterized in: by transferring the easily foaming neutralizing reaction of the hydrolyzate solution containing potassium methionine and carbon dioxide from the liquid phase to the gas phase, the problem of easily foaming in the neutralization in the liquid phase is fundamentally solved. Meanwhile, the oversaturation of methionine in the neutralization solution can be effectively controlled by mixing and diluting the hydrolyzate solution containing potassium methionine and the external circulation solution and then to be neutralized with the gas-phase carbon dioxide, thereby controlling the amount of new methionine crystal nucleus generated and enabling the methionine crystals to grow to obtain high bulk density methionine crystal products with larger particle diameters.

Effect of the Disclosure

The present disclosure has the following advantageous: the present disclosure uses a reaction solution containing potassium methionine to perform continuous neutralization crystallization in the DTB neutralization crystallizer having a gas phase neutralization section. The production process has good stability and high efficiency. The products obtained have stable quality. Therefore, the present disclosure is suitable for industrial production.

BRIEF DESCRIPTION OF THE DRAWINGS

FIG. 1 is an illustration of one embodiment of the DTB neutralization crystallizer having a gas phase neutralization section according to the present disclosure.

REFERENCE SIGNS

1 . . . liquid distributor
2 . . . gas distributor
3 . . . guide shell
4 . . . agitator arm
5 . . . rotary drum filter
6 . . . crystal mush pump
7 . . . external circulation pump
8, 9 . . . flow meter
10 . . . cooling heat exchanger
11 . . . external circulation outlet
12 . . . external circulation inlet
13 . . . $CO_2$ gas inlet
14 . . . mother liquor
15 . . . crystal
16 . . . hydrolysate solution
17 . . . boiling surface
18 . . . cylindrical baffle
19 . . . elutriation leg
A . . . gas-liquid contact neutralization region
B . . . clarification region
C . . . crystal deposition area
D . . . large crystal concentrating region The present disclosure is specifically described with reference to non-limiting embodiments as follows.

DETAILED DESCRIPTION

Example 1

The DTB neutralization crystallizer having a gas phase neutralization section of the present disclosure has the following configuration, including a liquid phase section having a volume of 1 $m^3$ which is designed according to the structure proportion of conventional DTB; a gas phase section having a volume of 0.6 $m^3$ in a shape of a cylindrical body with an elliptical sealed head, of which the diameter is 600 mm and the height is 2200 mm; a liquid distributor provided at the upper part; and a carbon dioxide gas distributor provided at the lower part.

In the DTB neutralization crystallizer having a gas phase neutralization section of the present disclosure, 0.9 $m^3$ of methionine saturated solution is added in advance, followed by 10 Kg of methionine crystal seed ground to having a diameter of no more than 10 micrometers. Then the crystallizer starts to stir at 100 rpm. Switch on the external circulation pump and adjust the flow rate of the external circulation solution entering the elutriation leg to 1.6 m$^3$/h and the flow rate of the external circulation solution to be mixed with the hydrolyzate solution containing potassium methionine to 10 m$^3$/h. After the circulation flow is stable, start circulation cooling to keep the temperature at 28° C. The carbon dioxide is introduced from the gas distributor till the pressure is up to 0.8 Mpa. At this moment, a hydrolyzate solution containing 19% of potassium methionine at 28° C. is introduced at a flow rate of 1 m$^3$/h (i.e., the retention time of 1 hour). After mixing with the external circulation material, the mixture is cooled by a cooler to 25° C. and enters the liquid distributor at the top of the crystallizer. The liquid is sprayed in the form of trickle into gas carbon dioxide for neutralization reaction to become a neutralization solution and fall into the liquid surface of the crystallizer. The temperature of the neutralization solution fallen into the liquid surface of the crystallizer has increased to 28° C. After mixing with stirring, the crystal seeds in the crystallizer grow. At the same time, a certain amount of new crystal seeds will be produced due to the oversaturation.

After the hydrolyzate solution containing potassium methionine has been introduced for 6 min, the crystal mush pump is switched on to feed methionine crystal mush into the rotary drum filter at a flow rate of 1.1 m$^3$/h for filtering and washing. Methionine products will be obtained after continuous fluidization desiccation of filter cake. After the operation has become totally stable (taking about 4 hours), methionine crystal products can be obtained at a yield of 112 Kg/h, of which the bulk density is 811 kg/m$^3$.

Foaming phenomenon is not observed during the whole process of continuous operation for 24 hours.

Example 2

In the DTB neutralization crystallizer having a gas phase neutralization section of Example 1, 0.9 m$^3$ of methionine saturated solution is added in advance, followed by 10 Kg of methionine crystal seed ground to having a diameter of no more than 10 micrometers. Then the crystallizer starts to stir at 200 rpm. Switch on the external circulation pump and adjust the flow rate of the external circulation solution entering the elutriation leg to and the flow rate of the external circulation solution to be mixed with the hydrolyzate solution containing potassium methionine to 20 m$^3$/h. After the circulation flow is stable, start circulation cooling to keep the temperature at 20° C. The carbon dioxide is introduced from the gas distributor till the pressure is up to 0.4 Mpa. At this moment, a hydrolyzate solution containing 19% of potassium methionine at 20° C. is introduced at a flow rate of 0.5 m$^3$/h (i.e., the retention time of 2 hours). After mixing with the external circulation material, the mixture is cooled by a cooler to 18° C. and enters the liquid distributor at the top of the crystallizer. The liquid is sprayed in the form of trickle into gas carbon dioxide for neutralization reaction to become a neutralization solution and fall into the liquid surface of the crystallizer. The temperature of the neutralization solution fallen into the liquid surface of the crystallizer has increased to 20° C. After mixing with stirring, the crystal seeds in the crystallizer grow. At the same time, a certain amount of new crystal seeds will be produced due to the oversaturation.

After the hydrolyzate solution containing potassium methionine has been introduced for 12 min, the crystal mush pump is switched on to feed methionine crystal mush into the rotary drum filter at a flow rate of 0.55 m$^3$/h for filtering and washing. Methionine products will be obtained after continuous fluidization desiccation of filter cake. After the operation has become totally stable (taking about 8 hours), methionine crystal products can be obtained at a yield of 57 Kg/h, of which the bulk density is 816 kg/m$^3$.

Foaming phenomenon is not observed during the whole process of continuous operation in 24 hours.

Example 3

In the DTB neutralization crystallizer having a gas phase neutralization section of Example 1, 0.9 m$^3$ of methionine saturated solution is added in advance, followed by 10 Kg of methionine crystal seed ground to having a diameter of no more than 10 micrometers. Then the crystallizer starts to stir at 400 rpm. Switch on the external circulation pump and adjust the flow rate of the external circulation solution entering the elutriation leg to 4 m$^3$/h and the flow rate of the external circulation solution to be mixed with the hydrolyzate solution containing potassium methionine to 10 m$^3$/h. After the circulation flow is stable, start circulation cooling to keep the temperature at 35° C. The carbon dioxide is introduced from the gas distributor till the pressure is up to 1.0 Mpa. At this moment, a hydrolyzate solution containing 19% of potassium methionine at 35° C. is introduced at a flow rate of 2 m$^3$/h (i.e., the retention time of 0.5 hour). After mixing with the external circulation material, the mixture is cooled by a cooler to 30° C. and enters the liquid distributor at the top of the crystallizer. The liquid is sprayed in the form of trickle into gas carbon dioxide for neutralization reaction to become a neutralization solution and fall into the liquid surface of the crystallizer. The temperature of the neutralization solution fallen into the liquid surface of the crystallizer has increased to 35° C. After mixing with stirring, the crystal seeds in the crystallizer grow. At the same time, a certain amount of new crystal seeds will be produced due to the oversaturation.

After the hydrolyzate solution containing potassium methionine has been introduced for 3 min, the crystal mush pump is switched on to feed methionine crystal mush into the rotary drum filter at a flow rate of 2.2 m$^3$/h for filtering and washing. Methionine products will be obtained after continuous fluidization desiccation of filter cake. After the operation has become totally stable (taking about 2 hours), methionine crystal products can be obtained at a yield of 221 Kg/h, of which the bulk density is 802 kg/m$^3$.

Foaming phenomenon is not observed during the whole process of continuous operation in 24 hours.

Example 4

In the DTB neutralization crystallizer having a gas phase neutralization section of Example 1, 0.9 m$^3$ of methionine saturated solution is added in advance, followed by 10 Kg of methionine crystal seed ground to having a diameter of no more than 10 micrometers. Then the crystallizer starts to stir at 50 rpm. Switch on the external circulation pump and adjust the flow rate of the external circulation solution entering the elutriation leg to 1.83 m$^3$/hand the flow rate of the external circulation solution to be mixed with the hydrolyzate solution containing potassium methionine to 16.66 m$^3$/h. After the circulation flow is stable, start circulation cooling to keep the temperature at 40° C. The carbon dioxide is introduced from the gas distributor till the pressure is up to 1.2 Mpa. At this moment, a hydrolyzate solution containing 19% of potassium methionine at 40° C. is introduced at a flow rate of 0.333 m³/h (i.e., the retention time of 3 hours). After mixing with the external circulation material, the mixture is cooled by a cooler to 39.5° C. and enters the liquid distributor at the top of the crystallizer. The liquid is sprayed in the form of trickle into gas carbon dioxide for neutralization reaction to become a neutralization solution and fall into the liquid surface of the crystallizer. The temperature of the neutralization solution fallen into the liquid surface of the crystallizer has increased to 40° C. After mixing with stirring, the crystal seeds in the crystallizer grow. At the same time, a certain amount of new crystal seeds will be produced due to the oversaturation.

After the hydrolyzate solution containing potassium methionine has been introduced for 18 min, the crystal mush pump is switched on to feed methionine crystal mush into the rotary drum filter at a flow rate of 0.366 m³/h for filtering and washing. Methionine products will be obtained after continuous fluidization desiccation of filter cake. After the operation has become totally stable (taking about 12 hours), methionine crystal products can be obtained at a yield of 36 Kg/h, of which the bulk density is 822 kg/m³.

Foaming phenomenon is not observed during the whole process of continuous operation in 24 hours.

Example 5

In the DTB neutralization crystallizer having a gas phase neutralization section of Example 1, 0.9 m³ of methionine saturated solution is added in advance, followed by 10 Kg of methionine crystal seed ground to having a diameter of no more than 10 micrometers. Then the crystallizer starts to stir at 500 rpm. Switch on the external circulation pump and adjust the flow rate of the external circulation solution entering the elutriation leg to 3.67 m³/h and the flow rate of the external circulation solution to be mixed with the hydrolyzate solution containing potassium methionine to 16.66 m³/h. After the circulation flow is stable, start circulation cooling to keep the temperature at 10° C. The carbon dioxide is introduced from the gas distributor till the pressure is up to 0.3 Mpa. At this moment, a hydrolyzate solution containing 15% of potassium methionine at 10° C. is introduced at a flow rate of 3.33 m³/h (i.e., the retention time of 0.3 hours). After mixing with the external circulation material, the mixture is cooled by a cooler to 5° C. and enters the liquid distributor at the top of the crystallizer. The liquid is sprayed in the form of trickle into gas carbon dioxide for neutralization reaction to become a neutralization solution and fall into the liquid surface of the crystallizer. The temperature of the neutralization solution fallen into the liquid surface of the crystallizer has increased to 10° C. After mixing with stirring, the crystal seeds in the crystallizer grow. At the same time, a certain amount of new crystal seeds will be produced due to the oversaturation.

After the hydrolyzate solution containing potassium methionine has been introduced for 1.8 min, the crystal mush pump is switched on to feed methionine crystal mush into the rotary drum filter at a flow rate of 3.67 m³/h for filtering and washing. Methionine products will be obtained after continuous fluidization desiccation of filter cake. After the operation has become totally stable (taking about 1.2 hours), methionine crystal products can be obtained at a yield of 268 Kg/h, of which the bulk density is 805 kg/m³.

Foaming phenomenon is not observed during the whole process of continuous operation in 24 hours.

Comparative Example

The experiment is carried out in the same way with Example 1, except the gas carbon dioxide is introduced into the crystallizer from the liquid phase.

In the DTB neutralization crystallizer having a gas phase neutralization section of Example 1, 0.9 m³ of methionine saturated solution is added in advance, followed by 10 Kg of methionine seed ground to having a diameter of no more than 10 micrometers. Then the crystallizer starts to stir at 100 rpm. Switch on the external circulation pump and adjust the flow rate of the external circulation solution entering the elutriation leg to 1.1 m³/h and the flow rate of the external circulation solution to be mixed with the hydrolyzate solution containing potassium methionine to 10 m³/h. After the circulation flow is stable, start circulation cooling to keep the temperature at 28° C. The carbon dioxide is introduced from the gas distributor till the pressure is up to 0.5 Mpa. At this moment, a hydrolyzate solution containing 19% of potassium methionine at 28° C. is introduced at a flow rate of 1 m³/h i.e., the retention time of 1 hour). After mixing with the external circulation material, the mixture is cooled by a cooler to 25° C. and enters the liquid distributor at the top of the crystallizer. The liquid falls in the form of trickle into the liquid surface of the crystallizer. After mixing with stirring, the liquid neutralizes with carbon dioxide dissolved in a liquid phase so that the crystal seeds in the crystallizer grow. At the same time, a certain amount of new crystal seeds will be produced due to the oversaturation.

After the hydrolyzate solution containing potassium methionine has been introduced for 6 min, the crystal mush pump is switched on to feed methionine crystal mush into the rotary drum filter at a flow rate of 1.1 m³/h for filtering and washing. Methionine products will be obtained after continuous fluidization desiccation of filter cake. After the operation has become totally stable (taking about 4 hours), methionine crystal products can be obtained at a yield of 111 Kg/h, of which the bulk density is 518 kg/m³.

During continuous operation in 24 hours, foaming phenomenon occurs in the whole process. Defoamer needs to be added continuously to maintain the continuous neutralization and crystallization process.

TABLE 1

| | Agitation rate (rpm) | Flow rate of external circulation solution to be mixed with hydrolysate solution (m³/h) | Temperature of external circulation solution (° C.) | Pressure of carbon dioxide (MPa) | Flow rate of hydrolyzate solution containing potassium methionine (m³/h) | Yield Kg/h | Bulk Density kg/m³ | Foaming |
|---|---|---|---|---|---|---|---|---|
| Example 1 | 100 | 10 | 28 | 0.8 | 1 | 112 | 811 | Not found |

TABLE 1-continued

|  | Agitation rate (rpm) | Flow rate of external circulation solution to be mixed with hydrolysate solution (m³/h) | Temperature of external circulation solution (° C.) | Pressure of carbon dioxide (MPa) | Flow rate of hydrolyzate solution containing potassium methionine (m³/h) | Yield Kg/h | Bulk Density kg/m³ | Foaming |
|---|---|---|---|---|---|---|---|---|
| Example 2 | 200 | 20 | 20 | 0.4 | 0.5 | 57 | 816 | Not found |
| Example 3 | 400 | 10 | 35 | 1.0 | 2 | 221 | 802 | Not found |
| Example 4 | 50 | 16.66 | 40 | 1.2 | 0.333 | 36 | 822 | Not found |
| Example 5 | 500 | 16.66 | 10 | 0.3 | 3.33 | 268 | 805 | Not found |
| Comparative Example 1 | 100 | 10 | 28 | 0.5 | 1 | 111 | 518 | obvious |

Referring to Table 1, in the production method of Comparative Example 1, the conditions for the operation is substantially the same with the method of the present application. Comparative Example 1 differs from the present application merely by introducing carbon dioxide in liquid phase, which result in obvious foaming phenomenon. Thus, the methionine crystal product obtained by Comparative Example 1 is affected; and the bulk density cannot meet with the requirement of the present application.

INDUSTRIAL APPLICABILITY

By continuous neutralization and crystallization using a reaction solution containing potassium methionine in a DTB neutralization crystallizer having a gas phase neutralization section, the present disclosure transfers neutralization reaction of the hydrolyzate solution containing potassium methionine and carbon dioxide which is easy to generate a foaming phenomenon from liquid phase to gas phase. Thus, the production process attains good stability and high efficiency. The product obtained has a stable quality. Therefore, the method of the present disclosure is suitable for industrial production.

What is claimed is:

1. A method for continuous preparation of high bulk density methionine crystals, comprising the following steps:
   (1) mixing a hydrolysate solution containing potassium methionine obtained from a reaction of 5-(β-methylmercaptoethyl)hydantoin and a potassium carbonate solution with an external circulation material from a DTB neutralization crystallizer having a gas phase neutralization section to form a mixture material; the mixture material entering a liquid distributor of a neutralization region in an upper part of the crystallizer after being cooled and being sprayed in the form of liquid droplet or trickle to gas-liquid contact area to carry out a neutralization reaction with carbon dioxide gas so that obtaining a neutralization solution containing methionine;
   (2) making the neutralization solution naturally fall into a crystallization region in the lower part of the crystallizer to form crystals in the crystallization region, and then making the crystals having larger particle diameters deposited into a elutriation leg in a deposition area in the middle part of the crystallization region;
   (3) feeding the methionine crystals in the elutriation leg through a crystal mush pump into a rotary drum filter to be subjected to separation, washing and drying to obtain methionine products;
   wherein the external circulation material is initially a saturated methionine solution and the bulk density of the high bulk density methionine crystals is at least 800 kg/m³.

2. The method for continuous preparation of high bulk density methionine crystals according to claim 1, wherein the crystallization process comprises growing on fine crystals already formed in the crystallization region to form crystals having larger particle diameters, while controlling the oversaturation to form new crystal nucleuses.

3. The method for continuous preparation of high bulk density methionine crystals according to claim 1, wherein in the deposition area in the middle part of the crystallization region, fine crystals and a part of the methionine solution enter an external circulation pipe for cooling and circulation; and a part of the external circulation materials is used to elutriate the crystals in the elutriation leg, while another part of the external circulation materials is used to be mixed with the hydrolyzate solution containing potassium methionine.

4. The method for continuous preparation of high bulk density methionine crystals according to claim 1, wherein the DTB neutralization crystallizer having a gas phase neutralization section has a gas phase space at an upper part, and a liquid distributor and a gas distributor are provided so that the liquid as a dispersed phase is subjected to a gas-liquid neutralization reaction in a carbon dioxide gas as a continuous phase.

5. The method for continuous preparation of high bulk density methionine crystals according to claim 1, wherein a volume ratio of the hydrolyzate solution containing potassium methionine in the outer circulation pipe of the DTB neutralization crystallizer having a gas phase neutralization section to the outer circulation material is 1:5-50, and the temperature of the material after being mixed is reduced by a cooler by 0.5-5° C.

6. The method for continuous preparation of high bulk density methionine crystals according to claim 1, wherein a volume ratio of the outer circulation material in the elutriation leg at the lower part of the DTB neutralization crystallizer having a gas phase neutralization section to the output volume of crystal mush is (1-5):1.

7. The method for continuous preparation of high bulk density methionine crystals according to claim 1, wherein an agitation rate in the crystallization region of the DTB neutralization crystallizer having a gas phase neutralization section is 50-500 rpm.

8. The method for continuous preparation of high bulk density methionine crystals according to claim 1, wherein the temperature of the crystallization region of the DTB neutralization crystallizer having a gas phase neutralization section is 10-40° C.

9. The method for continuous preparation of high bulk density methionine crystals according to claim 1, wherein the hydrolyzate solution containing potassium methionine stays in the neutralization crystallizer for 0.3-3 hours.

10. The method for continuous preparation of high bulk density methionine crystals according to claim 1, wherein a pressure of the gas-phase carbon dioxide in the DTB neutralization crystallizer having a gas phase neutralization section is 0.3-1.2 Mpa.

11. A DTB neutralization crystallizer having a gas phase neutralization section for continuous preparation of high bulk density methionine crystals, comprising:

(1) a liquid distributor for forming the liquid droplets or trickles of mixed liquor containing potassium methionine and a gas distributor for supplying carbon dioxide gas that are provided in a neutralization region at an upper part, (2) a liquid guide shell and a stirrer provided in the middle part, (3) a crystal deposition area provided at a lower part, which includes an elutriation leg for depositing crystals, (4) an external circulation system for recycling potassium methionine solution in a crystallization region, and a part of the solution being supplied to the elutriation leg while another part of the same being mixed with the hydrolyzate solution containing potassium methionine and then circulating supply to a material inlet of the neutralization crystallizer, and wherein the bulk density of the high bulk density methionine crystals is at least 800 kg/m$^3$.

12. The DTB neutralization crystallizer having a gas phase neutralization section according to claim 11, further comprising a rotary drum filter for separating and washing crystal mush from the elutriation leg.

* * * * *